United States Patent [19]

Okabe et al.

[11] 4,191,708

[45] Mar. 4, 1980

[54] PROCESS FOR PREPARING AND PURIFYING P-PHENYLENEDIAMINE

[75] Inventors: Hiromichi Okabe, Hirakata; Kiyomi Kishimoto, Kurashiki; Fumio Ohi, Toyonaka, all of Japan

[73] Assignee: Sumitomo Chemical Company, Limited, Osaka, Japan

[21] Appl. No.: 868,435

[22] Filed: Jan. 10, 1978

[30] Foreign Application Priority Data

Jan. 28, 1977 [JP] Japan .................................. 52-8958

[51] Int. Cl.$^2$ ............................................. C07C 85/26
[52] U.S. Cl. ................................... 260/582; 260/205; 260/208
[58] Field of Search ................ 260/582, 578, 205, 208

[56] References Cited

U.S. PATENT DOCUMENTS

| | | | |
|---|---|---|---|
| 2,708,680 | 5/1955 | Richmond | 260/582 |
| 2,809,884 | 10/1957 | Ratje | 260/582 X |
| 3,093,649 | 6/1963 | Ratje et al. | 260/582 X |
| 3,149,162 | 9/1964 | Gardner et al. | 260/582 |

FOREIGN PATENT DOCUMENTS

| | | | |
|---|---|---|---|
| 328210 | 4/1930 | United Kingdom | 260/582 |
| 909054 | 10/1962 | United Kingdom | 260/582 |
| 1430366 | 3/1976 | United Kingdom | 260/582 |

OTHER PUBLICATIONS

Fierz-David et al., "Dye Chemistry", 5th Ed., pp. 34-40 (1949).
Beilstein's Handbook, 2nd Supplement, Band 16, pp. 147-151.
Handbook of Chemistry & Physics, 58th Ed., p. C-133.

*Primary Examiner*—John Doll
*Attorney, Agent, or Firm*—Stevens, Davis, Miller & Mosher

[57] ABSTRACT

Highly pure p-phenylenediamine can advantageously be prepared on a commercial scale by separating and removing o-aminoazobenzene produced as a by-product in the step of producing p-aminoazobenzene, from the product mixture before p-aminoazobenzene is reduced in a process for preparing p-phenylenediamine which comprises preparing p-aminoazobenzene from aniline by way of diazoaminobenzene and then reducing p-aminoazobenzene.

6 Claims, No Drawings

PROCESS FOR PREPARING AND PURIFYING P-PHENYLENEDIAMINE

The present invention relates to an improvement in a process for preparing highly pure p-phenylenediamine. More particularly, the invention pertains to an improvement in a process for preparing p-phenylenediamine, which process comprises preparing diazoaminobenzene from aniline, preparing p-aminoazobenzene by the rearrangement reaction of diazoaminobenzene in the presence of an acid catalyst, and then reducing p-aminoazobenzene to obtain p-phenylenediamine.

p-Phenylenediamine has long been used in the rubber chemical industry, dye industry and pigment industry in a large amount and recently serves an important use as a starting material for heat-resistant polyamide resins.

As a representative process for preparing p-phenylenediamine, the following processes have heretofore been known:
(1) Amination of p-dihalogenobenzene or p-halogenoaniline with ammonia
(2) Reduction of p-dinitrobenzene or p-nitroaniline
(3) Reduction of p-aminoazobenzene The process (1) has a defect in that the yield of p-phenylenediamine is reduced by the formation of tar due to severe reaction conditions. The process (2) is restricted as to the starting material since the preparation of p-nitroaniline as a starting material is accompanied by much trouble. On the other hand, the process (3) is not restricted by a starting material but can produce p-phenylenediamine in a high yield under mild reaction conditions. Therefore, the process (3) is widely carried out on a commercial scale.

However, the process (3) has a defect as a commercial process for preparing highly pure p-phenylenediamine usable as a starting material, for example, for heat-resistant polyamide resins because, as is described in British Pat. No. 1,430,366, several % by weight of o-phenylenediamine as a by-product is unavoidably contained in the final product, and it is generally very troublesome to separate the o-phenylenediamine from the product in a satisfactory purification yield.

It is, therefore, the principal object of the present invention is to avoid the difficulties heretofore encountered in the preparation of p-phenylenediamine.

It is a further object to provide a process for preparing p-phenylenediamine, which is not only simple in operation but also produces a product of high purity.

Another object of the present invention is to provide an improved process for preparing p-phenylenediamine from p-aminoazobenzene.

The other objects and advantages of the invention will be apparent from the following description.

As a result of the present inventors' extensive studies on a commercial process for preparing highly pure p-phenylenediamine according to the process (3), it has now been found that p-aminoazobenzene obtained by the rearrangement reaction of diazoaminobenzene in the presence of an acid catalyst contains several % by weight of o-aminoazobenzene, that the o-aminoazobenzene can be separated by a comparatively simple means, and that p-phenylenediamine substantially freed from o-phenylenediamine can advantageously be prepared on a commercial scale without purifying the p-phenylenediamine product by separating the o-aminoazobenzene at this stage and then carrying out usual reduction of the remaining pure p-aminoazobenzene.

According to the present invention, there is provided an improved process for preparing p-phenylenediamine by preparing p-aminoazobenzene from aniline by way of diazoaminobenzene and then reducing the p-aminoazobenzene, characterized by separating and removing o-aminoazobenzene produced as a by-product in the step of preparing p-aminoazobenzene, from the reaction product containing p-aminoazobenzene and o-aminoazobenzene as a by-product before p-aminoazobenzene is reduced.

As a method for separating and removing the o-aminoazobenzene by-product contained in the p-aminoazobenzene product obtained by the rearrangement reaction of diazoaminobenzene, which operation is an essential feature of the present invention, for example, extraction, crystallization, etc. may be used. Among these methods, crystallization treatment is most preferable from a commercial point of view. In any one of these methods, the selection of a solvent is an important factor. It is required that the solvent show a difference between dissolving power for o-aminoazobenzene and p-aminoazobenzene and to be able to separate the two isomers efficiently from each other. As such a solvent suitable for the objects of the present invention, petroleum solvents having a boiling point ranging from 50° to 150° C., cyclohexane, and cyclohexanes substituted by an alkyl group having 1 to 3 carbon atoms are preferably used. Specific examples of such preferable solvents include petroleum benzine, ligroin, cyclohexane, methylcyclohexane, ethylcyclohexane, and a mixture thereof.

The amount of o-aminoazobenzene contained in the p-aminoazobenzene product in the present invention is not limited.

In order to carry out the present purification efficiently and economically, however, the o-isomer content is 20% by weight or less, and preferably 10% by weight or less, based on the weight of the p-isomer.

The process of the present invention will be explained in more detail in due order.

Aniline as a starting material is first converted to diazoaminobenzene by diazotization with an alkali metal nitrite, for example, sodium nitrite, and a subsequent coupling reaction according to a known method. These reactions are usually carried out in the presence of excess aniline. Thereafter, a rearrangement reaction with an acid catalyst such as hydrochloric acid or sulfuric acid is carried out to obtain p-aminoazobenzene. The acid can be used as it is or as its amine salt such as aniline hydrochloride.

The rearrangement reaction is carried out usually in the presence of excess aniline according to a usual method, for example, the method described in British Pat. No. 1,430,366. The reaction product is obtained as an about 30% aniline solution. However, the aniline content of the product solution is not critical in the present invention.

An alkali metal hydroxide such as sodium hydroxide or potassium hydroxide is added to the aniline solution to neutralize the remaining acid catalyst, and aniline is then removed and recovered by distillation.

On the distillation of aniline, it is not necessarily required to recover all of the aniline, but it is desirable that the amount of aniline contained in the reaction product at this stage is 7% by weight or less, and preferably 3% by weight or less, based on the weight of the distillation residue.

The residual oily reaction product after removal of excess aniline contains p-aminoazobenzene and small amount (usually about 4 to 8% by weight) of o-aminoazobenzene and shows physical properties an oil at a temperature of 70° C. or more.

Thereafter, the above-defined solvent is added to the oily product and the resulting mixture is heated to 80° to 90° C. to form a complete solution, which is in turn cooled to produce p-aminoazobenzene crystals. Then, the crystals are collected by filtration. The suitable amount of the solvent used is generally 2 to 8 times, and preferably 3 to 5 times, the weight of the oily product.

With regard to the case wherein ligroin is used as the solvent, the crystallization operation will be explained below in more detail, but the case wherein the other solvents are used will also be explained likewise.

Ligroin previously heated to 80° C. is added to the oily product kept at 70° C. or more. The resulting mixture is heated to dissolve the mixture in ligroin completely. When the amount of ligroin used is 4 to 5 times the weight of the oily product, the completely dissolved state can be maintained at 80° to 85° C.

Thereafter, crystallization is carried out by cooling the solution to 0° to 35° C., and preferably 5° to 25° C., in 1 to 10 hours, and preferably 2 to 5 hours, with slowly stirring.

It is unnecessary to control or restrict the temperature gradient on cooling, the apparatus used, etc. in the crystallization. The crystallization can be carried out under a wide range of conditions. Purification effect and recovery percentage are less affected by crystallization time or crystallization method.

When the inside temperature reaches an appointed temperature, the cooled mixture is filtered to obtain crystals. The collected crystals are then washed with 0.3 to 1.5 times, and preferably 0.4 to 0.6 times the weight of crystals with ligroin.

Thus, a cake of p-aminoazobenzene having a very low content (usually 0.3% by weight or less) of the o-isomer can be obtained at a high recovery percentage of 97% or more. The term "recovery percentage" used herein has the meaning as represented by the following equation:

$$\text{Recovery percentage (\%)} = \frac{\text{Weight of p-aminoazo-benzene in cake}}{\text{Weight of p-aminoazo-benzene before crystallization}} \times 100$$

The crystallization of the present invention can be repeated to obtain p-aminoazobenzene substantially freed from o-aminoazobenzene.

The thus obtained highly pure p-aminoazobenzene is reduced with a hydrogenation catalyst such as Pt, Pd, Ni, etc. in a dissolving solvent such as alcohols, etc., for example, according to Lessie H. Andrews et al's method [J. Amer. Chem. Soc., Vol. 56, page 1411 (1934)]. Thus, p-phenylenediamine and aniline are obtained. Aniline can usually be separated by distillation and the desired highly pure p-phenylenediamine can be recovered. Of course, not only the above-mentioned method but also all the other known reduction methods can be used for obtaining p-phenylenediamine by reduction of p-aminoazobenzene.

The following examples, in which all parts and % are expressed by weight unless otherwise indicated, will serve to illustrate the present invention in more detail, but the present invention is not limited to the examples.

EXAMPLE 1

A mixture of 130 parts of aniline and 28.1 parts of 32% hydrochloric acid is cooled to 15° C. Thereto are added 24.2 parts of ice and 13.8 parts of sodium nitrite at a temperature up to 40° C. with stirring. If the inside temperature exceeds 40° C., ice is further added. When nitrous acid is no more detectable by the starch-iodine reaction, the reaction is completed. The reaction mixture is allowed to stand and is then separated into an aqueous layer and an aniline layer.

To the aniline layer is added 9.7 parts of aniline hydrochloride in one hour. Isomerization reaction is carried out by stirring the mixture at 40° C. for 4 hours.

After completing the isomerization reaction, the reaction mixture is heated to 50° C. in 30 minutes and is then maintained at the temperature for one hour. The reaction mixture is mixed with 33.5 parts of a 33% aqueous caustic soda solution, and the resulting mixture is stirred at 45° C. for 4 hours. After standing, the mixture is separated into an aqueous layer and an aniline layer. Thus, 132 parts of the aniline layer are obtained.

A weight ratio of p-aminoazobenzene to o-aminoazobenzene in the aniline layer is 93:7. Aniline is removed by steam distillation. The residue is allowed to stand and are then separated into an aqueous layer and an oil layer. Thus, 40 parts of the oil layer is obtained. As a result of analysis, it is found that the amount of aniline contained in the oil layer is 0.5%.

To the oil layer maintained at 80° C. is added 160 parts of ligroin previously heated to 70° C. The temperature of the resulting mixture is maintained at 80° to 85° C. for 20 minutes. Thus, the mixture becomes a uniform solution. When the solution is gradually cooled, the crystals begin to separate at 60° to 65° C. Cooling is further continued with slowly stirring. When the inside temperature reaches 15° C., cooling is stopped and the crystals are separated from the mother liquor by filtration.

The time required for the crystallization is 2.5 hours. The crystals separated are washed with 20 parts of ligroin to obtain 41.5 parts of a cake (solid content 90%). p-Aminoazobenzene and o-aminoazobenzene contents in the cake are found to be 99.7% and 0.3%, respectively, by liquid chromatography. Recovery percentage is 98%.

Into an autoclave with an agitating means are charged 41.5 parts of said crystals, 100 parts of methanol and 0.6 part of Raney nickel. Reduction reaction is carried out at 70° to 75° C. and at a hydrogen pressure of 25 kg/cm$^2$ gauge.

Absorption of hydrogen is completed in 2 hours. At this time point, aminoazobenzenes have disappeared completely.

The reaction mixture is cooled to room temperature, and the catalyst is removed by filtration. Methanol and aniline are separated and recovered by distillation at reduced pressure. The resulting residue is distilled at a pressure of 40 mmHg in a stream of nitrogen to obtain 20.0 parts of p-phenylenediamine containing 0.25% by weight (measured by gas chromatography) of o-phenylenediamine. The yield of p-phenylenediamine based on sodium nitrite is 91.0%.

EXAMPLE 2

In the same manner as in Example 1, 40.0 parts of a mixture of p-aminoazobenzene and o-aminoazobenzene are obtained. The mixture is completely dissolved in 160 parts of a 1:1 mixed solvent of cyclohexane and ligroin at 85° C. The solution is cooled to 15° C. in 2 hours with stirring. The crystals separated are filtered and washed with 20 parts of said mixed solvent to obtain 40 parts of crystals. p-Aminoazobenzene and o-aminoazobenzene contents in the crystals are found to be 99.7% and 0.3%, respectively, by liquid chromatography. Recovery percentage is 97.5%.

The crystals are subjected to reduction with 0.6 part of Raney nickel and 100 parts of aniline and after-treatment in the same manner as in Example 1. Aniline is then recovered and the resulting residue is distilled at reduced pressure. Thus, 20.1 parts of p-phenylenediamine having a purity of 99.8% are obtained. The yield of p-phenylenediamine based on sodium nitrite is 91.4%.

EXAMPLE 3

In the same manner as in Example 1, 40.0 parts of a mixture of p-aminoazobenzene and o-aminoazobenzene are obtained.

The mixture is dissolved in 140 parts of methylcyclohexane at 85° C., and the resulting solution is cooled to 10° C. in 2.5 hours with stirring. The crystals separated are filtered and washed with 20 parts of methylcyclohexane to obtain 40 parts of crystals.

p-Aminoazobenzene and o-aminoazobenzene contents in the crystals are found to be 99.7% and 0.3%, respectively, by liquid chromatography. Recovery percentage is 98.0%.

The crystals are reduced with 70 parts of methanol and 0.3 part of a 10% Pd-carbon catalyst at 65° to 70° C. and at a hydrogen pressure of 25 kg/cm$^2$ gauge.

Absorption of hydrogen is completed in 1.5 hours. The reaction mixture is cooled and the catalyst is removed by filtration. Methanol used as a solvent and aniline produced as a by-product in the reduction reaction are recovered by distillation. Subsequent distillation at reduced pressure (40 mmHg) gives 20.2 parts of p-phenylenediamine having a purity of 99.8%. The yield of p-phenylenediamine based on sodium nitrite is 91.9%.

EXAMPLE 4

41.5 Parts of a cake (solid content being 90%, p- and o-aminoazobenzene contents being 99.7% and 0.3%, respectively), which is obtained in the same manner as in Example 1, is further mixed with 150 parts of ligroin, and the mixture is heated to 80° to 85° C. to dissolve crystals completely. When the solution is gradually cooled with slow stirring, the crystals begin to separate at about 65° C. Cooling is further continued with slow stirring to lower the inner temperature to 10° C., and then the crystals are separated from the mother liquor by filtration. The time required for the crystallization is 3 hours. The crystals separated are washed with 20 parts of ligroin to obtain 40.0 parts of p-aminoazobenzene crystals. An o-aminoazobenzene content in the crystals is below the limit (0.1%) detectable by liquid chromatography. Recovery percentage in this second crystallization is 98.0%.

The resulting crystals are reduced in the same manner as in Example 1 to obtain 19.5 parts of a reduction product. The o-phenylenediamine content in the product is below the limit (0.1%) detectable by gas chromatography, and the yield of p-phenylenediamine based on sodium nitrite is 89.2%.

What is claimed is:

1. In a process for preparing p-phenylenediamine by preparing p-aminoazobenzene from aniline by way of diazoaminobenzene and then reducing the p-aminoazobenzene, the improvement characterized by separating and removing o-aminoazobenzene produced as a by-product in the step of preparing p-aminoazobenzene, from the reaction product containing p-aminoazobenzene and o-aminoazobenzene as a by-product by crystallization from a solvent before p-aminoazobenzene is reduced.

2. A process according to claim 1, wherein said crystallization treatment is carried out by the use of a solvent selected from the group consisting of petroleum solvents having a boiling point ranging from 50° to 150° C., cyclohexane and cyclohexanes substituted by an alkyl group having 1 to 3 carbon atoms.

3. A process according to claim 2, wherein said solvent is ligroin or cyclohexane.

4. A process according to claim 2, wherein the amount of said solvent used is 2 to 8 times the weight of the reaction product.

5. A process according to claim 4, wherein the amount of said solvent used is 3 to 5 times the weight of the reaction product.

6. In a process for preparing p-phenylenediamine comprising the steps of, (1) reacting a diazotized aniline with aniline in the presence of excess aniline to obtain a diazoaminobenzene-containing aniline solution, (2) subjecting the solution to a rearrangement reaction in the presence of an acid catalyst to obtain a p-aminoazobenzene-containing aniline solution, (3) treating the aniline solution with an alkali to neutralize the acid catalyst remaining in the aniline solution, (4) removing the excess aniline to give an oily product, and (5) subjecting the oily product to a reduction using a hydrogenation catalyst in a solvent to convert p-aminoazobenzene into p-phenylenediamine, the improvement which comprises heating the oily product obtained in the step (4) with at least one solvent selected from the group consisting of petroleum solvents having a boiling point ranging from 50° to 150° C., cyclohexane and cyclohexanes substituted by an alkyl group having 1 to 3 carbon atoms, to form a solution, cooling the solution, separating a crystal portion of p-aminoazobenzene substantially freed from a by-product, o-aminoazobenzene, and then subjecting the p-aminoazobenzene substantially freed from the by-product to the reduction in the step (5), whereby p-phenylenediamine substantially freed from a by-product, o-phenylenediamine, is obtained.

* * * * *